United States Patent
Sidi et al.

4,022,906
May 10, 1977

[54] BIOCIDAL COMPOSITIONS CONTAINING BICYCLIC POLYOXYMETHYLENEOXAZOLIDINES

[75] Inventors: Henri Sidi, Paramus; Hilding R. Johnson, Wayne, both of N.J.

[73] Assignee: Tenneco Chemicals, Inc., Saddle Brook, N.J.

[22] Filed: Aug. 25, 1975

[21] Appl. No.: 607,738

Related U.S. Application Data

[62] Division of Ser. No. 519,885, Oct. 31, 1974, Pat. No. 3,952,000, which is a division of Ser. No. 447,797, March 4, 1974, Pat. No. 3,890,264.

[52] U.S. Cl. .................. 424/272; 260/45.8 NZ; 106/15 R
[51] Int. Cl.² ............... A01N 9/22; A01N 9/28; C08K 5/34
[58] Field of Search ............ 260/45.8 NZ, 307 F, 260/307 FA; 424/272

[56] References Cited
UNITED STATES PATENTS

| | | | |
|---|---|---|---|
| 3,738,992 | 6/1973 | Frump | 260/307 FA |
| 3,838,164 | 9/1974 | Himics | 260/307 FA |
| 3,890,264 | 6/1975 | Sidi et al. | 260/45.8 NZ |
| 3,905,928 | 9/1975 | Sidi et al. | 260/45.8 NZ |

Primary Examiner—V. D. Turner
Attorney, Agent, or Firm—Evelyn Berlow

[57] ABSTRACT

Biocidal compositions useful in controlling the growth of bacteria and fungi in aqueous surface coatings are aqueous solutions that contain from 20 percent to 80 percent by weight of bicyclic polyoxymethyleneoxazolidines having the structural formula

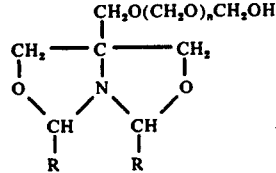

wherein each R represents hydrogen, alkyl of 1 to 6 carbon atoms, phenyl, halophenyl, or $-(CH_2O)_mCH_2OH$; $m$ represents a number in the range of 0 to 2; and $n$ represents a number in the range of 1 to 4.

6 Claims, No Drawings

BIOCIDAL COMPOSITIONS CONTAINING BICYCLIC POLYOXYMETHYLENEOXAZOLIDINES

This is a division of our copending application Ser. No. 519,885, which was filed on Oct. 31, 1974 and is now U.S. Pat. No. 3,952,000 and which is a division of our copending application Ser. No. 447,797, which was filed on Mar. 4, 1974 and is now U.S. Pat. No. 3,890,264.

This invention relates to biocidal compositions that are aqueous solutions that contain from 20 to 80 percent by weight of bicyclic polyoxymethyleneoxazolidines and that are useful in controlling the growth of bacteria and fungi in aqueous surface-coating compositions.

It is well known in the art that paints and varnishes often have inadequate resistance to the action of microorganisms. Some of these coating compositions, such as enamels and house paints, contain as their resinous binders drying oils, oleoresinous varnishes, or alkyd resins, which are subject to attack by fungi and bacteria. Others, for example, aqueous dispersions of water-insoluble synthetic linear polymers, generally contain as plasticizers and thickeners materials that have their origin in animal or vegetable sources and that render the compositions susceptible to mildew. The resulting deterioration of the surface-coating compositions seriously hinders their full scale utilization, particularly in those areas and in those applications that are conducive to such attack.

Various biocidal materials have been suggested for use in surface-coating compositions, but none has proven entirely satisfactory in this application. Some do not provide the required prolonged protection against attack by microorganisms, while others undergo sulfide staining and still others hydrolyze in alkaline aqueous paint systems or separate from the applied coating by migration, volatilization, or leaching after the coating has been spread in a thin layer over the surface to be protected. Some biocidal materials cause the coating compositions to gel or impart color or odor to them.

This invention relates to biocidal compositions that are of particular value in controlling the growth of bacteria and fungi in aqueous surface-coating compositions. These compositions, which are thoroughly compatible with the resinous binders that are commonly used in surface-coating compositions and which are resistant to sulfide staining, provide excellent and prolonged resistance to deterioration resulting from attack by bacteria, fungi, and other microorganisms without adversely affecting the color, pH, viscosity, and other physical properties of the surface-coating compositions.

The biocidal compositions of this invention are aqueous solutions that contain from about 20 percent to 80 percent by weight of bicyclic polyoxymethyleneoxazolidines having the structural formula

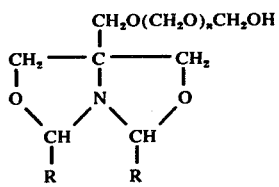

wherein each R represents hydrogen, alkyl of 1 to 6 carbon atoms, phenyl, halophenyl, or $-(CH_2O)_mCH_2OH$; $m$ represents a number in the range of 0 to 2; and $n$ represents a number in the range of 1 to 4.

Illustrative of the bicyclic polyoxymethyleneoxazolidines that may be present in the biocidal compositions are the following: 5-[hydroxymethyl-di(oxymethylene)]-1-aza-3,7-dioxabicyclo(3.3.0)-octane, 5-[hydroxymethyl-tri(oxymethylene)]-1-aza-3,7-dioxabicyclo-(3.3.0)octane, 2-phenyl-5-[hydroxymethyl-tetra(oxymethylene)]-1-aza-3,7-dioxabicyclo(3.3.0)octane, 2,8-bis(α-chloroethyl)-5-[hydroxymethyl-penta(oxymethylene)]-1-aza-3,7-dioxabicyclo(3.3.0)-octane, 2,8-bis(p-chlorophenyl)-5-[hydroxymethyl-tri(oxymethylene)]-1-aza-3,7-dioxabicyclo(3.3.0octane, 2hydroxymethyl-5-[hydroxymethyl-tetra(oxymethylene)]-1-aza-3,7-dioxabicyclo(3.3.0)octane, 2,8-bis(2-ethylbutyl)-5-[hydroxymethyl-tri(oxymethylene)]-1-aza-3,7-dioxabicyclo(3.3.0)octane, and 2,8-bis(hydroxymethyl-5-[hydroxymethyl-di(oxymethylene)]-1-aza-3,7-dioxabicyclo(3.3.0)octane. One or more of the bicyclic polyoxymethyleneoxazolidines may be present in the biocidal compositions.

The biocidal compositions that are most effective in protecting surface-coating compositions are those that contain bicyclic compounds in which the total number of oxymethylene ($-CH_2O-$) units in one or more of the substituents on the oxazolidine ring is not greater than six. While compositions that contain compounds having more than six oxymethylene units in their ring substituents are very effective in controlling the growth of bacteria and fungi, they tend to be somewhat unstable in the surface-coating compositions and to impart to them the odor of formaldehyde. Examples of the preferred bicyclic compounds include polyoxymethyleneoxazolidines in which i. the substituent in the 5-position is $-(CH_2O(CH_2O)_{1-4}CH_2OH$ and the substituents in the 2- and 8-positions are hydrogen, alkyl, phenyl, or halophenyl;

ii. the substituent in the 5-position is $-CH_2OCH_2OCH_2OH$, that in the 2-position is $-(CH_2O)_{0-2}CH_2OH$, and that in the 8-position is hydrogen, alkyl, phenyl, or halophenyl; and iii. the substituent in the 5-position is $-CH_2O(CH_2O)_{1-2}CH_2OH$ and the substituents in the 2- and 8-positions are $-CH_2OH$.

The biocidal compositions of this invention may be prepared by any suitable and convenient procedure. For example, they may be prepared by dissolving one or more of the bicyclic polyoxymethyleneoxazolidines in water. Alternatively, they may be prepared by the reaction of the appropriate oxazolidine with formaldehyde and/or paraformaldehyde in aqueous solution, or by the reaction of an aminoalcohol with formaldehyde and/or paraformaldehyde and optionally another aldehyde in aqueous solution. When an aqueous formaldehyde solution is used, the reactions are preferably carried out at ambient temperature; when paraformaldehyde or a mixture of aqueous formaldehyde and paraformaldehyde is used, it is preferred that the reaction be carried out at a temperature between about 30° C. and 100° C.

Among the aminoalcohols that can be reacted with formaldehyde and, if desired, another aldehyde in aqueous solution to form the novel biocidal compositions are 2-amino-1,3-propanediol, 2-amino-2-methyl- 1,3-propanediol, 2-amino-2-ethyl-1,3-propanediol, 2-amino-2-butyl-1,3-propanediol, and tris(hydroxymethyl)aminomethane. The aminoalcohol is reacted with an aqueous formaldehyde solution or a mixture of an aqueous formaldehyde solution and a second aldehyde that is an aliphatic aldehyde such as acetaldehyde, α-chloroacetaldehyde, propionaldehyde, butyraldehyde, or 2-ethylbutyraldehyde, an aromatic aldehyde such as benzaldehyde, p-chlorobenzaldehyde, or 2,4-dichlorobenzaldehyde, a dialdehyde such as glyoxal, succinaldehyde, or glutaraldehyde, or a mixture of these aldehydes.

The aqueous solutions of polyoxymethyleneoxazolidines resulting from the reactions previously described may be used without purification or additional treatment other than adjustment of the concentration of the biocidal component to the desired level to protect surface-coating compositions from attack by bacteria and fungi. In addition to costing less than the purified polyoxymethyleneoxazolidines and being easier to incorporate into aqueous surface-coating compositions, the aqueous solutions, which contain 20 percent to 80 percent and preferably 40 percent to 60 percent by weight of one or more of the aforementioned polyoxymethyleneoxazolidines, provide better biocidal activity for a given concentration of the polyoxymethyleneoxazolidine in the surface-coating composition. Unlike most other aqueous surface-coating compositions that contain a biocide, the surface-coating compositions to which the aqueous polyoxymethyleneoxazolidine solutions have been added tend to become lighter in color on aging.

The biocidal compositions of this invention can be used to impart bacterial and fungal resistance to a wide variety of surface-coating compositions including both water-based and organic solvent-based coating systems.

The biocidal compositions can be used in aqueous surface-coating compositions that contain about 10 percent to 60 percent by weight of a water-insoluble, film-forming, resinous binder that is an oleoresinous binder, a synthetic linear addition polymer, or a mixture of these binders. The useful aqueous dispersions of synthetic linear addition polymers are ordinarily prepared by the emulsion polymerization of ethylenically-unsaturated monomers. Illustrative of these polymers are polyvinyl acetate; polyvinyl butyrate; polyvinyl chloride; copolymers of vinyl acetate with vinyl chloride or acrylonitrile; copolymers of vinyl chloride with vinylidene chloride; polyethylene; polyisobutylene; polystyrene; copolymers of styrene with maleic anhydride or butadiene; copolymers of acrylonitrile with butadiene; copolymers of methacrylic acid esters of alcohols having 1 to 8 carbon atoms with vinyl acetate, vinyl chloride, acrylonitrile, or styrene; copolymers of acrylic acid esters of alcohols having 1 to 8 carbon atoms with vinyl acetate, vinyl chloride, acrylonitrile, or styrene; and mixtures thereof. Suitable oleoresinous binders include drying oils, such as linseed oil, tung oil, soybean oil, dehydrated castor oil, safflower oil, or fish oil; bodied drying oils; blends of drying oils or bodied drying oils with a resin component such as limed rosin, an ester gum, or phenolic resin; oleoresinous varnishes formed by heating one of the aforementioned resins with one or more drying oils or bodied drying oils; alkyd resins, which are resinous products resulting from the reaction of a polyhydric alcohol, such as pentaerythritol or glycerol, with a dicarboxylic acid, such as phthalic anhydride, and fatty acids; and mixtures thereof.

They can also be used in organic solvent-based systems that contain an oleoresinous binder as hereinbefore defined.

The addition to surface-coating compositions of an amount of the biocidal composition that will provide as little as 0.1 percent by weight of one or more of the bicyclic polyoxymethyleneoxazolidines will bring about an appreciable improvement in the resistance of the composition to attack by fungi and bacteria. Amounts of the biocidal composition that improve 3 percent or more of the polyoxymethyleneoxazolidines can be used, but these larger amounts ordinarily do not provide further improvement in the properties of the surface-coating compositions and for this reason are not usually used. The amount of the biocidal composition that will provide optimum protection for a surface-coating composition depends upon such factors as the choice of the biocidal compound, the choice of resinous binder and other ingredients of the composition and the amount of each of these materials that is used, and the application for which the coating composition is intended. In most cases an amount of the biocidal composition that will provide 1 percent to 2 percent of polyoxymethyleneoxazolidine, based on the weight of the surface-coating composition, is used to protect surface-coating compositions from attack by fungi. An amount of the biocidal composition that will provide 0.1 percent to 0.5 percent of a polyoxymethyleneoxazolidine, based on the weight of the surface-coating composition, is preferably incorporated into aqueous surface-coating compositions to protect them from attack by bacteria.

In addition to the resinous binder and the biocidal composition, the surface-coating compositions may contain various auxiliary materials, such as pigments, extenders, solvents, dyes, defoaming agents, driers, thickeners, emulsifiers, plasticizers, other biocides, and the like in the amounts ordinarily used for these purposes.

The invention is further illustrated by the following examples.

EXAMPLE 1

A mixture of 60.5 grams (0.5 mole) of tris(hydroxymethyl)aminomethane, 121.5 grams (1.5 moles) of 37% aqueous formaldehyde solution, and 31.6 grams (1.0 mole) of 95% paraformaldehyde was stirred and heated at its reflux temperature until a homogeneous solution was obtained. The solution was cooled and filtered. There was obtained 213 grams of a clear yellow solution that contained 43.1% of water and 56.9% of solids. The pH of an 0.1 M solution of the product was 6.6. The product was shown by NMR, IR, and GC analysis of its silyl ethers to be a mixture of 5-hydroxymethyl-1-aza-3,7-dioxabicyclo(3.3.0)octane, 5-hydroxymethoxymethyl-1-aza-3,7-dioxabicyclo(3.3.0)octane, and 5-hydroxymethylpolyoxymethylene-1-aza-3,7-dioxabicyclo(3.3.0)octanes having the structural formula

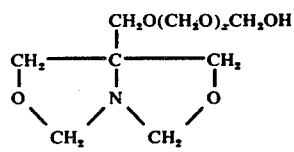

wherein x represents numbers in the range of 1 to 3.

EXAMPLE 2

A mixture of 60.5 grams (0.5 mole) of tris(hydroxymethyl)aminomethane, 121.5 grams (1.5 moles) of 37% aqueous formaldehyde solution, and 47.3 grams (1.5 moles) of 95% paraformaldehyde was stirred and heated at its reflux temperature until a homogeneous solution was obtained. The solution was cooled and filtered. There was obtained 229.3 grams of a clear yellow solution that contained 40.1% of water and 59.9% of solids. The pH of an 0.1 M solution of the product was 6.6. The product was shown by NMR, IR, and GC analysis of its silyl ethers to be a mixture containing about 20% of 5-hydroxymethyl-1-aza-3,7-dioxabicyclo(3.3.0)octane, 37% of 5-hydroxymethoxymethyl-1-aza-3,7-dioxabicyclo(3.3.0)octane, 14% of 5-[hydroxymethyl-di(oxymethylene)]-1-aza-3,7-dioxabicyclo(3.3.0)octane, 21% of 5-[hydroxymethyl-tri(oxymethylene)]-1-aza-3,7-dioxabicyclo(3.3.0)octane, and 8% of 5-[hydroxymethyl-tetra(oxymethylene)]-1-aza-3,7-dioxabicyclo(3.3.0)octane.

EXAMPLE 3

A mixture of 29.0 grams (0.2 mole) of 5-hydroxymethyl-1-aza-3,7-dioxabicyclo(3.3.0)octane and 32.4 grams (0.4 mole) of 37% aqueous formaldehyde solution was stirred at ambient temperature until a homogeneous solution was obtained. The product was an aqueous solution that contained 26.1% of water and 73.9% of 5-[hydroxymethyl-di(oxymethylene)]-1-aza-3,7-dioxabicyclo(3.3.0)octane. The pH of an 0.1 M solution of the product was 6.9.

EXAMPLE 4

A. A polyvinyl acetate latex paint was prepared by mixing together the following materials:

|  | Parts by Weight |
|---|---|
| Water | 481.5 |
| 25% Aqueous solution of sodium salt of maleic anhydride/diisobutylene copolymer | 24 |
| Potassium pyrophosphate | 3 |
| Long chain fatty acid alkanolamide | 9 |
| Defoamer | 6 |
| Ethylene glycol | 75 |
| 1¼% Aqueous solution of hydroxyethylcellulose | 375 |
| Aqueous emulsion containing 55% of polyvinyl acetate | 1299 |
| Diethyl ether of diethylene glycol | 30 |
| Titanium dioxide | 690 |
| Talc | 345 |
| Calcium metasilicate | 150 |

This paint had the following properties as determined by standard paint testing procedures:

| Viscosity | 65 K.U. |
|---|---|
| Brookfield Viscosity (No. 4 spindle, 60 rpm) | 800 cps. |
| pH | 7.8 |

| Yellowness Index | 3.0 |
|---|---|

Small amounts of the biocidal compositions of this invention or of comparative biocides were added to portions of this paint.

B. An acrylic latex paint was prepared by mixing together the following materials:

|  | Parts by Weight |
|---|---|
| Water | 168 |
| Alkyl aryl ether surfactant | 6 |
| 25% Aqueous solution of sodium salt of maleic anhydride/diisobutylene copolymer | 27 |
| Defoamer | 12 |
| 2% Aqueous solution of hydroxyethylcellulose | 300 |
| Ethylene glycol | 60 |
| Titanium dioxide | 750 |
| Mica (waterground) | 90 |
| Calcium carbonate | 375 |
| Ammonium hydroxide (28%) | 6 |
| Aqueous dispersion containing 46% acrylic ester copolymer (66% ethyl acrylate, 32.5% methyl acrylate, and 1.5% acrylic acid) | 1642 |

This paint had the following properties:

| Viscosity | 720 K.U. |
|---|---|
| Brookfield Viscosity (No. 4 spindle, 60 rpm) | 1250 cps. |
| pH | 9.2 |
| Yellowness Index | 2.6 |

Small amounts of the biocidal compositions of this invention or of comparative biocides were added to portions of this paint.

C. An exterior house paint was prepared by mixing together the following materials:

|  | Parts by Weight |
|---|---|
| Basic lead carbonate | 288 |
| Zinc oxide | 232 |
| Titanium dioxide (rutile) | 149 |
| Talc | 260 |
| Linseed oil | 242 |
| Bodied linseed oil | 114 |
| Mineral spirits | 114 |
| Antiskinning agent | 2 |
| Manganese naphthenate (6%) | 2.27 |
| Lead naphthenate (24%) | 11.3 |

Small amounts of the biocidal compositions of this invention or of comparative biocides were added to portions of this paint.

D. The polyvinyl acetate latex paint, the acrylic latex paint, and the oil-based paint were evaluated by means of an agar diffusion assay. In this test, agar is inoculated with the test organism, the treated paint is placed in a well cut from the agar, and after incubation at 28° C. and 85–95% relative humidity, the activity of the biocide is measured by zones of inhibition. The biocidal compounds tested and the results obtained are given in the table that follows. In this table

| | ZO | = | Zone of inhibited growth in mm. |
|---|---|---|---|
| | O | = | No zone of inhibition; no growth |
| | Tr | = | Trace zone of inhibited growth |
| | — | = | Not tested |
| Bacteria | A | = | Mixed paint spoilage strains |
| | B | = | Pseudomonas aeruginosa |
| | C | = | Aerobacter aerogenes |

-continued

|  | Fungi | D | = | Pullularia pullulans |
|---|---|---|---|---|
|  |  | E | = | Penicilliun crustosum |
|  |  | F | = | Aspergillus niger |

Table

Activity of Polyoxymethyleneoxazolidines as Biocides in Paints

| Biocide | Paint | Test Level* | Effect on Liquid Paint | | | | Biocidal Activity | | | | | |
|---|---|---|---|---|---|---|---|---|---|---|---|---|
|  |  |  | pH | Odor | Color | ViscosityA | Bacteria | | | Fungi | | |
|  |  |  |  |  |  |  | A | B | C | D | E | F |
| Product of Ex. 1 | PVA | 2 | 7.3 | None | None | None | ZO-20 | ZO-10 | ZO-14 | ZO-20 | ZO-9 | ZO-2 |
|  |  | 1 | 7.4 | " | " | " | ZO-17 | ZO-8 | ZO-10 | ZO-10 | ZO-8 | ZO-1 |
|  |  | 0.5 | 7.4 | " | " | " | ZO-15 | ZO-5 | ZO-8 | Zo-5 | ZO-5 | 0 |
|  |  | 0.1 | 7.4 | " | " | " | ZO-7 | ZO-3 | ZO-1 | 0 | 0 | 0 |
|  | Acrylic | 2 | 7.7 | " | " | Gelled | ZO-24 | ZO-9 | ZO-10 | ZO-19 | ZO-7 | ZO-1 |
|  |  | 1 | 7.9 | " | " | None | ZO-11 | ZO-2 | ZO-4 | ZO-3 | ZO-4 | Tr |
|  |  | 0.5 | 8.5 | " | " | " | ZO-5 | Tr | ZO-1 | 0 | 0 | 0 |
|  |  | 0.1 | 0.1 | " | " | " | 0 | 0 | 0 | 0 | 0 | 0 |
|  | Oil | 2 | — | " | " | " | — | — | — | ZO-4 | ZO-3 | ZO-2 |
| Product of Ex. 2 | PVA | 2 | 7.3 | None | None | None | ZO-22 | ZO-14 | ZO-14 | ZO-30 | ZO-11 | ZO-3 |
|  |  | 1 | 7.4 | " | " | " | ZO-18 | ZO-8 | ZO-14 | ZO-10 | ZO-8 | ZO-2 |
|  |  | 0.5 | 7.4 | " | " | " | ZO-15 | ZO-7 | ZO-11 | ZO-5 | ZO-5 | Tr |
|  |  | 0.1 | 7.4 | " | " | " | ZO-7 | ZO-4 | ZO-5 | Tr | ZO-1 | 0 |
|  | Acrylic | 2 | 7.6 | " | " | " | ZO-20 | ZO-9 | ZO-13 | ZO-21 | ZO-9 | ZO-3 |
|  |  | 1 | 7.8 | " | " | " | ZO-12 | ZO-4 | ZO-7 | ZO-5 | ZO-4 | Tr |
|  |  | 0.5 | 8.4 | " | " | " | ZO-7 | ZO-2 | ZO-1 | Tr | 0 | 0 |
|  |  | 0.1 | 9.1 | " | " | " | Tr | 0 | 0 | 0 | 0 | 0 |
|  | Oil | 2 | — | " | " | " | — | — | — | ZO-7 | ZO-5 | ZO-3 |
| Product of Ex. 3 | PVA | 2 | 6.8 | None | None | Gelled | ZO-15 | ZO-8 | ZO-10 | ZO-20 | ZO-8 | ZO-1 |
|  |  | 1 | 7.2 | " | " | None | ZO-15 | ZO-9 | ZO-9 | ZO-14 | ZO-5 | Tr |
|  |  | 0.5 | 7.3 | " | " | " | ZO-13 | ZO-7 | ZO-8 | ZO-8 | ZO-2 | Tr |
|  |  | 0.1 | 7.5 | " | " | " | ZO-6 | ZO-2 | Tr | 0 | 0 | 0 |
|  | Acrylic | 2 | 7.3 | " | " | " | ZO-14 | ZO-7 | ZO-9 | ZO-15 | ZO-8 | ZO-2 |
|  |  | 1 | 7.5 | " | " | " | ZO-11 | ZO-5 | ZO-8 | ZO-8 | ZO-3 | 0 |
|  |  | 0.5 | 8.1 | " | " | " | ZO-5 | ZO-1 | ZO-3 | 0 | 0 | 0 |
|  |  | 0.1 | 8.6 | " | " | " | Tr | 0 | 0 | 0 | 0 | 0 |
|  | Oil | 2 | — | " | " | " | — | — | — | ZO-7 | ZO-7 | ZO-1 |
| Comparative Examples |  |  |  |  |  |  |  |  |  |  |  |  |
| 5-Hydroxymethyl-1-aza- | PVA | 2 | 7.5 | None | None | None | ZO-3 | ZO-4 | ZO-1 | ZO-4 | ZO-2 | 0 |
| 3,7-dioxabicyclo | Acrylic | 2 | 8.4 | " | " | " | ZO-11 | ZO-3 | ZO-4 | ZO-6 | 0 | 0 |
| (3.3.0)octane (51.2% aqueous solution) | Oil | 2 | — | " | " | " | — | — | — | 0 | Tr | 0 |
| S-13 (Dow | PVA | 2 | 7.5 | None | None | None | ZO-13 | 0 | 0 | ZO-14 | ZO-19 | ZO-12 |
| Chemical Co.) | Acrylic | 2 | 9.1 | " | " | " | ZO-13 | 0 | 0 | ZO-20 | ZO-11 | ZO-5 |
|  | Oil | 2 | — | " | " | " | — | — | — | ZO-20 | ZO-10 | ZO-6 |
| Bis(phenylmercuric)- | PVA | 2 | 7.0 | None | None | None | ZO-19 | ZO-11 | ZO-9 | ZO-13 | ZO-10 | ZO-15 |
| dodecenyl succinate | Acrylic | 2 | 9.0 | " | " | " | ZO-17 | ZO-13 | ZO-8 | ZO-10 | ZO-3 | ZO-10 |
| (Super Ad-it) · (Tenneco Chemicals, Inc.) | Oil | 2 | — | " | " | " | — | — | — | ZO-17 | ZO-6 | ZO-14 |
| None | PVA | — | 7.5 | None | None | None | 0 | 0 | 0 | 0 | 0 | 0 |
|  | Acrylic | — | 9.3 | " | " | " | 0 | 0 | 0 | 0 | 0 | 0 |
|  | Oil | — | — | " | " | " | — | — | — | 0 | 0 | 0 |

*% of biocidal compound(s) added

The superiority as biocides for surface-coating compositions of biocidal compositions of this invention over a closely-related substituted oxazolidine is apparent from a comparison of the biocidal data for the products of Examples 1-3 with those for 5-hydroxymethyl-1-aza-3,7-dioxabicyclo(3.3.0)octane. The products of Examples 1 and 2, which are aqueous solutions containing mixtures of substituted oxazolidines that include the comparator 5-hydroxymethyl-1-aza-3,7-dioxabicyclo(3.3.0)octane as well as 5-hydroxymethylpolyoxymethylene-1-aza-3,7-dioxabicyclo(3.3.0)-octanes, were substantially more effective against bacteria and fungi than the comparator. Similarly, it is shown in the table that the product of Example 3 is more active at the 0.5% level in the PVA paint and at the 1% level in the acrylic paint than the comparator at the 2% level.

What is claimed is:

1. A biocidal composition for use in inhibiting the growth of bacteria and fungi in aqueous surface-coating compositions that is an aqueous solution containing 20 percent to 80 percent by weight of a biocidal component that comprises a bicyclic polyoxymethyleneoxazolidine having the structural formula

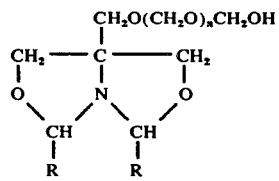

wherein each R represents hydrogen, alkyl of 1 to 6 carbon atoms, phenyl, halophenyl, or —(CH$_2$O)$_m$CH$_2$OH; $m$ represents a number in the range of 0 to 2; and $n$ represents a number in the range of 1 to 4.

2. A biocidal composition as defined in claim 1 that contains 40 percent to 60 percent of said biocidal component.

3. A biocidal composition as defined in claim 1 wherein the biocidal component comprises a polyoxymethyleneoxazolidine having the structural formula

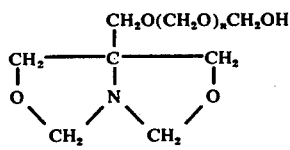

wherein *n* represents a number in the range of 1 to 4.

4. A biocidal composition as defined in claim 3 wherein the biocidal component comprises 5-[hydroxymethyl-di(oxymethylene)]-1-aza-3,7-dioxabicyclo(3.3.0)octane.

5. A biocidal composition as defined in claim 3 wherein the biocidal component comprises 5-[hydroxymethyl-tri(oxymethylene)]-1-aza-3,7-dioxabicyclo(3.3.0)octane.

6. A biocidal composition as defined in claim 3 wherein the biocidal component comprises 5-[hydroxymethyl-tetra(oxymethylene)]-1-aza-3,7-dioxabicyclo(3.3.0)octane.

* * * * *